United States Patent
Dugger, III (12)

(10) Patent No.: US 6,391,282 B1
(45) Date of Patent: *May 21, 2002

(54) ANTIHISTAMINE SPRAYS AND OINTMENTS FOR RELIEF OF DELAYED CONTACT DERMATITIS

(75) Inventor: Harry A. Dugger, III, Flemington, NJ (US)

(73) Assignee: Flemington Pharmaceutical Corp., Flemington, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/967,569

(22) Filed: Nov. 10, 1997

(51) Int. Cl.$^7$ .................................................. A61K 9/12
(52) U.S. Cl. ........................ 424/45; 424/400; 424/401; 514/357; 514/862
(58) Field of Search ............................ 424/45, 47, 400, 424/401; 514/357, 862

(56) References Cited

U.S. PATENT DOCUMENTS

| 4,863,970 | A | * | 9/1989 | Patel et al. ................ 514/784 |
| 4,906,488 | A | * | 3/1990 | Pera ........................... 426/573 |
| 5,660,859 | A | * | 8/1997 | Cody et al. ................. 424/451 |
| 5,693,608 | A | * | 12/1997 | Bechgaard ...................... 514/2 |
| 5,708,033 | A | * | 1/1998 | Modak et al. ............... 374/494 |
| 5,833,999 | A | * | 11/1998 | Trinh et al. ................. 424/401 |
| 5,888,520 | A | * | 3/1999 | Toma et al. ................. 424/401 |
| 6,203,817 | B1 | * | 3/2001 | Coymier et al. ............ 424/464 |

FOREIGN PATENT DOCUMENTS

| EP | 0189861 | * | 8/1986 |
| GB | 2098865 | * | 2/1983 |
| JP | 20258730 | * | 10/1990 |
| JP | 8-81368 | * | 3/1996 |
| WO | WO 97/02273 | * | 1/1997 |

OTHER PUBLICATIONS

Milks etal Practical Veterinary Pharmacology pp 270, 1949.*
Goodman & GilMan Pharmacological Basis of Therapeutics 4th Edition p643, 1970.*

* cited by examiner

Primary Examiner—Neil S. Levy
(74) Attorney, Agent, or Firm—Selitto, Behr & Kim

(57) ABSTRACT

It has been found that certain antihistamines can mediate the delayed dermatitis and in particular that caused by poison ivy and poison sumac or poison oak. Especially useful are antihistamines having a high degree of intrinsic activity as shown by their low oral dosage as antihistamine (0.1–10, suitably 1–2 mg), which can be topically administered at a sufficiently high active concentration to be effective in the treatment of allergic reactions. Compositions and methods of utilizing such compositions for these purposes are disclosed.

1 Claim, No Drawings

ANTIHISTAMINE SPRAYS AND OINTMENTS FOR RELIEF OF DELAYED CONTACT DERMATITIS

FIELD OF THE INVENTION

Anti histamine compositions for relief of delayed contact dermatites,

BACKGROUND OF THE INVENTION

Allergies are divided into four types as discussed in Goodman & Gilman, "The Pharmacological Basis of Therapeutics" as follows:

Allergic responses have been divided into four general categories, based on the mechanism of immunological involvement (Coombs and Gell, in Gell, Coombs and Lachmann, eds., *Clinical Aspects of Immunology*, Blackwell, Oxford, p 761, 1975).

Type I, or anaphylactic, reactions in human beings are mediated by IgE antibodies. The Fc portion of IgE can bind to receptors on mast cells and basophils. If the Fab portion of the antibody molecule then binds antigen, various mediators (histamine, leukotrienes, prostaglandins) are released and cause vasodilatation, edema, and an inflammatory response. The main targets of this type of reaction are the gastrointestinal tract (food allergies), the skin (urticaria and a topic dermatitis), the respiratory system (rhinitis and asthma), and the vasculature (anaphylactic shock). These responses tend to occur quickly after challenge with an antigen to which the individual has been sensitized and are termed immediate hypersensitivity reactions.

Type II, or cytolytic, reactions are mediated by both IgG and IgM antibodies and usually are attributed to their ability to activate the complement system. The major target tissues for cytolytic reactions are the cells in the circulatory system. Examples of type II allergic responses include penicillin-induced hemolytic anemia, methyldopa-induced autoimmune hemolytic anemia, quinidine-induced thrombocytopenic purpura, sulfonamide-induced granulocytopenia, and hydralazine- or procainamide-induced systemic lupus erythematosus. Fortunately, these autoimmune reactions to drugs usually subside within several months after removal of the offending agent.

Type III, or Arthus, reactions are mediated predominantly by IgG; the mechanism involves the generation of antigen-antibody complexes that subsequently fix complement. The complexes are deposited in the vascular endothelium, where a destructive inflammatory response called serum sickness occurs. This phenomenon contrasts with the type II reaction, in which the inflammatory response is induced by antibodies directed against tissue antigens. The clinical symptoms of serum sickness include urticarial skin eruptions, arthralgia or arthritis, lymphadenopathy, and fever. These reactions usually last for 6 to 12 days and then subside after the offending agent is eliminated. Several drugs, such as sulfonamides, penicillins, certain anticonvulsants, and iodides, can induce serum sickness. Stevens-Johnson syndrome, such as that caused by sulfonamides, is a more severe form of immune vasculitis. Symptoms of this reaction include erythema multiform, arthritis, nephritis, CNS abnormalities, and myocarditis.

Type IV, or delayed-hypersensitivity, reactions are mediated by sensitized T lymphocytes and macrophages. When sensitized cells come in contact with antigen, an inflammatory reaction is generated by the production of lymphokines and the subsequent influx of neutrophils and macrophages. An example of type IV or delayed hypersensitivity is the contact dermatitis caused by poison ivy.

DISCUSSION OF THE PRIOR ART

Most treatments for the delayed allergic reaction, as opposed to palliative treatment for itching and drying of the secretions from the lesion, are hormonal or anti-inflammatory in nature. Examples are cortisone, chloroxine, coal tar, dexamethasone, neomycin, hydrocortisone, ketoconizole. High potency fluorinated corticosteroids if applied in the earlier stages of the rash where the skin is red but not yet blistered can be useful in limited areas to materially decrease the evolution of the dermatitis and prevent the apparent spread of the disease. The use of these preparations is limited because of their high potency and the real possibility of systemic effects especially if used on large areas where the skin is broken or ulcerative. Systemic corticosteroids and andrenocorticotropic hormone work well but must be given by injection. The use of these agents is usually limited to those cases that are in stage 5–7 (see below).

The reaction to delayed hypersensitivity such as poison ivy can be broken down into several stages. The following is the system used to grade the response:

| Stage of reaction | |
|---|---|
| 1 | Erythema with itching |
| 2 | Erythema with edema and itching |
| 3 | Erythema with edema and beginning vesiculation involving less than 25% of the site |
| 4 | Same as 3 but involving 25–50% of the site |
| 5 | Same as 3 but involving 50–75% of the site |
| 6 | Same as 3 but vesicles confluent in a circular pattern on the site |
| 7 | Erythema, edema, vesiculation and evidence of ulcerative breakdown |

Only one preparation, Caladryl® for the treatment of poison ivy, poison oak and poison sumac containing an antihistamine, diphenhydramine hydrochloride, as one of its components has been marketed in the USA to date. This product is ineffective because of the weak antihistaminic effect in the treatment of these irritations except for some relief of itching and as a drying agent due to the presence of Calamine in the formulation. Several ointments are on the market in Europe, but they are not indicated for the treatment of poison ivy, poison oak or poison sumac as these plants are not found in Europe. From their formulations (usually contain 0.05% antihistamine), as found on their package inserts, they would be no more effective in the treatment of poison ivy, poison oak and poison sumac than Caladryl®. To have the desired effect one needs to deliver a very active antihistamine at a high concentration to a local area.

SUMMARY OF THE INVENTION

Contrary to the above teachings that the Type IV or delayed hypersensitivity is mediated by sensitized T lymphocytes and macrophages, that it has been found an antihistamine and in particular clemastine or chlorpheniramine can mediate the delayed dermatitis and in particular that caused by poison ivy and poison sumac or poison oak. Especially useful are antihistamines having a high degree of intrinsic activity as shown by their low oral dosage as antihistamine (0.1–10, suitably 1–2 mg), which can be topically administered at a sufficiently high active concentration to be effective in the treatment of delayed allergic reactions. Applied in this manner in the early stages of the irritation to the developing delayed reaction, these products have the property, in the correct formulation, of stopping the reaction to poison ivy, poison oak and poison sumac.

The early stage of the irritation is characterized by the beginning of itching, appearance of redness and of small red welts. After application of the preparation the itching stops and the redness recedes. The skin returns to its nearly normal condition within 12–36 hours.

Even if applied after major blisters appear, the reaction to the allergen stops—the blisters collapse and the itching stops. Some time is still required for the healing of the skin after the reaction to the allergen stops.

Poison ivy treatments to be effective must be a massive intervention because by the time the rash is apparent the allergic response because of the delayed reaction is well on the way to being a major problem. This massive intervention in our case is a very potent antihistamine as judged by the oral dose given in a large amount (0.5% ointment or 1–2 mg in a spray) to a local area.

The effective antihistamines, most suitably, clemastine or chlorpheniramine can be delivered to the site of the lesion either as an ointment to be massaged into the skin by hand, or as a spray also to be massaged into the skin by hand. If the fumarate or other salt is to be used, a pump spray and polar solvents would be preferred. If the free base should be used as the active ingredient, either a pump spray, or an aerosol spray using a propellant can be employed. After applying the spray, the resulting fine layer of liquid can be massaged into the skin by hand.

The only limit on the solvent to be used for the spray or ointment is that it must be compatible with topical applications, and at least one of them should have the properties of a dermal penetration enhancer. These ointments can be packaged in soft gelatin capsules for one time use, in foil packs or in tubes for one time use or in tubes for multiple use.

In the use of potent antihistamines, the preferred packaging amount is a small unit to avoid the possibility that the patients, in their irritated state, may overdose. Thus side effects may result either topically or systemically as antihistamines may undergo some absorption through the skin, especially if it is broken or ulcerated.

DESCRIPTION OF THE PREFERRED EMBODIMENTS

In the preferred embodiments of the present invention there are provided spray composition for topical administration of antihistaminically active compounds which have a level of activity, when orally administered of 0.1–10 mg/dose. Where these active compounds is soluble in a pharmacologically acceptable polar solvent, the spray comprises, in weight % of total composition: polar solvent 77–98%, active compound 1–20%. Where the active compound is soluble in a pharmacologically acceptable non-polar solvent the spray composition comprises in weight % of total composition: a pharmaceutically acceptable propellant, suitably a $C_{3-8}$ hydrocarbon of a linear or branched configuration 45–93%, non-polar solvent 5–55%, and active compound 1–20%.

While the invention is in no way limited thereto, as active compounds clemastine, chlorpheniramine, astemazole, triprolidine, trimeprazine, methdilazine, hydroxyzine, dextromorphan, citirizine and loratadine in their nonionized form or as the pharmaceutically acceptable salts thereof, have been found most suitable.

Additionally, the spray compositions may comprise, by weight of total composition: aromatizing agent 1–15%, suitably synthetic or natural oil of peppermint, oil of spearmint, rose oil, citrus oil, fruit aromas and combinations thereof.

As preferred polar solvents there may be mentioned low molecular weight polyethyleneglycols (PEG) of 200–600 MW, $C_2$–$C_8$ mono- and polyalcohols, and alcohols of $C_7$–$C_8$ hydrocarbons of a linear or branched configuration. Most suitable in this group are aqueous ethylene glycol and aqueous ethanol.

Preferred polar spray compositions include polar solvent 77–98%, clemastine 0.1–10%, aromatizing agent 1–15% and polar solvent 75–99%, chlorpheniramine 0.1–10%, aromatizing agent 1–15%.

Preferred among the propellants are propane, N-butane, iso-butane, N-pentane, iso-pentane, or neo-pentane, and mixtures thereof. Most suitably, wherein the propellant is N-butane or iso-butane it has a water content of no more than 0.2% and oxidizing agents, reducing agents, and Lewis acids or bases content in a concentration of less than 0.1%.

As non polar solvents, there may be utilized ($C_2$–$C_{24}$) fatty acid ($C_2$–$C_6$) esters, $C_7$–$C_{18}$ hydrocarbons of a linear or branched configuration, and $C_2$–$C_6$ alkanoyl esters, and triglycerides of said fatty acids. Most suitably, miglyol.

Suitable non polar spray compositions include propellant 45–93%, non-polar solvent 5–55%, clemastine 0.1–10%, aromatizing agent 1–15%; propellant 45–93%, non-polar solvent 5–55%, chlorpheniramine 0.1–10%, aromatizing agent 1–15%; propellant 45–93%, non-polar solvent 5–55%, citirizine 0.1–10%, aromatizing agent 1–15%; and propellant 45–93%, non-polar solvent 5–55%, astemazole 0.1–10%, aromatizing agent 1–15%.

There are also provided lotion compositions, including ointments, creams, emulsions and the like, for topical administration of antihistaminically active compounds such as the general group and preferred species listed above, wherein the composition comprises in weight % of total composition: solvent 15–99%, active compound 0.1–85%. These compositions may be provided as individual dosage forms as gelatin capsules in which case it is desirable that the composition contains less than 10% of water to avoid deterioration of the capsule.

If desired, the foregoing aromatizing agents may also be used. As solvents, the polar and non polar solvents listed above are also operative.

The occurrence of delayed contact dermatitis in a mammal may be modified or reduced by administering an antihistaminically pharmacologically active compound to said mammal having been exposed to a delayed contact dermatitis causing substance, by spraying the potentially affected skin location thereof with any of the forgoing spray compositions, or applying any of the foregoing lotion compositions.

Drug Substance Properties: Antihistamines which may be used are limited to those that exhibit antihistamine properties at a very low dose (0.1 to 10 mg) and that are soluble enough in the solvent of choice to lead to solutions having a concentration of 1.0 to 20.0% w/w. Suitably, there may be used clemastine, chlorpheniramine, astemazole, triprolidine, trimeprazine, methdilazine, hydroxyzine, dextromorphan, citirizine and loratadine in their nonionized form or as the pharmaceutically acceptable salts thereof. The antihistamine of choice would be clemastine hydrogen fumarate or clemastine base. A second first choice would be chlorpheniramine hydrochloride or base.

Formulation of AEROSOL SPRAYS for Topical Application

The preferred Propellant Properties for these sprays may be expressed as follows: Low molecular weight hydrocarbons such as ethane, propane, n-butane, iso-butane, n-pentane, iso-pentane, and neo-pentane or mixtures of these hydrocarbons such that a reasonable pressure obtained in the container. If the pressure is too high, there will be a danger that the container or seals of the valve will burst, and if too low there will not be enough pressure to expel the drug solution from the container especially at lower temperatures. Preferred are n-butane or iso-butane as single propellant gases. The propellant should be free of oxidizing agents <0.1%, reducing agents <0.1% acid or base (Lewis acids of bases), water content in the range 0.1–0.2%.

The preferred Solvent Properties may be expressed as follows: Nonpolar, $C_{7-18}$ hydrocarbons and their alcohols, esters of fatty acids, fatty acid triglycerides such as migylol, must be miscible with the propellant such that one phase is formed at temperatures 0–40° C. One of the solvents acts as a dermal penetration enhancer.

Optionally, there may be used Aroma Agents such as: Oil of peppermint, oil of spearmint, oil of wintergreen, citrus oils, both synthetic and natural as well as oil of rose or other perfumes, which are normally used in creams and lotions.

The following general formulation has been developed for the aerosol sprays: Propellant: 45–93% by weight, Solvent: 5–55% by weight, Drug substance: 1.0–20% by weight, and Flavoring agents: 1–15% by weight. A metered dose valve is suitably employed that delivers 25–150 microliters of spray per activation.

Formulation of PUMP SPRAYS for Topical Application

The preferred Solvent Properties are as follows: For salts and such polar drugs, one can use water, low molecular weight alcohol's (preferable ethanol), polyethylene glycols (PEG) in the range 200–600, low molecular weight ketones such as acetone and combinations thereof. At least one of the solvents acts as a dermal penetration enhancer.

Optionally, there may be employed Aroma agents such as: Oil of peppermint, oil of spearmint, oil of wintergreen, citrus oils, both synthetic and natural as well as oil of rose or other perfumes which are normally used in creams and lotions.

The following general formulation has been developed for pump sprays: For antihistamine salts as drug substances: Polar solvent :77–98% by weight, Drug substance: 1–20% by weight; Flavoring agents : 0–15% by weight.

Antihistamine Ointments for Topical Application

The preferred Solvent Properties for the Solution Formulation are: Solvents such as polyethylene glycol's (PEG) of the 400–1000 molecular weight, but preferred are those in the 400–600 range, fatty acid esters and triglycerides. Low molecular weight alcohols and poly-alcohols can also be used. One of the solvents acts as a dermal penetration enhancer. If the ointment or gel is packaged as a soft gelatin capsule, glycerin and water should be used sparingly as they will migrate into the shell and weaken the shell or make it tacky.

Optionally Aroma Agents may be employed such as: Oil of peppermint, oil of spearmint, oil of wintergreen, citrus oils, both synthetic and natural. Oil of rose or other perfumes normally used in creams and lotions may be used.

The following general formulations have been developed for antihistamine ointments: Solvent: 15–99% by weight, Drug substance: 0.1–85% by weight, and Flavoring agents: 1–3% by weight.

EXAMPLES

Example 1

A specific formulation for clemastine base as an aerosol spray

| | |
|---|---|
| Clemastine (base) | 337 mg |
| Iso-butane | 4.8 gm |
| Miglyol | 2.6 gm |
| Oil of wintergreen | 0.5 mg |

1 or 2 activations of 50 microliters each would be used to deliver 1–2 mg of clemastine base.

In accordance with the above formulation, but where, in place of clemastine base there is utilized chlorpheniramine, astemazole, triprolidine, trimeprazine, methdilazine, hydroxyzine, dextromorphan, citirizine and loratadine, a spray of similar activity is obtained, however actual dosage amounts of the active substance will vary.

Example 2

A specific formulation for clemastine fumarate as a pump spray

| | |
|---|---|
| Clemastine fumarate | 134 mg |
| Ethanol | 7.0 ml |
| Water | 3.0 ml |
| Oil of Rose | 0.5 ml |

Two activations of 50 microliters each would be used to deliver 1.34 mg of the salt.

In accordance with the above formulation, but where, in place of clemastine fumarate there is utilized chlorpheniramine, astemazole, triprolidine, trimeprazine, methdilazine, hydroxyzine, dextromorphan, and loratadine free bases as well as their respective salts, a spray of similar activity is obtained, however actual dosage amounts of the active substance will vary.

Example 3

A specific formulation for citirizine hydrochloride as a pump spray

| | |
|---|---|
| Citirizine hydrochloride | 850 mg |
| Ethanol | 7.0 ml |
| Water | 3.0 ml |
| Oil of Rose | 0.5 ml |

Two activations of 50 microliters each would be used to deliver 7.7 mg of the salt.

In accordance with the above formulation, but where, in place of clemastine fumarate there is utilized chlorpheniramine, astemazole, triprolidine, trimeprazine, methdilazine, hydroxyzine, dextromorphan, and loratadine as their respective salts, a spray of similar activity is obtained, however actual dosage amounts of the active substance will vary.

Example 4

| A specific formulation for clemastine salt as a lotion | |
|---|---|
| Clemastine fumarate | 1.34 mg |
| Polyethylene glycol | 242.00 mg |
| Glycerin | 12.00 mg |
| Water | 14.00 mg |
| Oil of wintergreen | 5.00 mg |

Applications of 275–550 mg of the ointment would deliver 1.34–2.68 25 mg of salt.

In accordance with the above formulation, but where, in place of clemastine fumarate there is utilized chlorpheniramine, astemazole, triprolidine, trimeprazine, methdilazine, hydroxyzine, dextromorphan, citirizine and loratadine as their respective salts, a lotion of similar activity is obtained.

Example 5

Treatment of Poison ivy exposure with composition of Example 3

On Day 1 subject became exposed to poison ivy on the back of the knees and between the thighs. On Day 4 severe itching was noted and the composition was applied. In ten minutes the itching disappeared. Three hours later, inflammation but no itching was noted, the composition was reapplied. Six hours later, inflammation was still noted, but no itching, further application of composition. After further six hours, a further application was made. This was repeated 12 hours later (morning of Day 6). The exposure location on the thigh was noted to start drying, that behind the knees was blistering ad suppurating but not spreading. Applications were repeated six eleven and sixteen hours later. On Day 7, application was made in the early morning and nine hours later. No itching noted, thigh area was clear, knee area ceased suppurating, one blister remaining. Morning of Day 8, everything was drying up.

What is claimed is:

1. A method of controlling the occurrence of delayed contact dermatitis in a mammal by administering an antihistaminically pharmacologically active compound to said mammal having been exposed to a delayed contact dermatitis causing substance derived from poison oak, poison ivy or poison sumac, by applying to the location thereof an antihistaminically effective amount of a lotion composition selected from the group consisting of clemastine, chlorpheniramine, astemazole triprolidine, trimeprazine, methdilazine, hydroxyzine, citirizine and loratadine in their nonionized form or as the pharmaceutically acceptable salts thereof said active compound being dissolved in a lotion composition provided that where the said active compound is soluble in a pharmacologically acceptable polar solvent selected from the group consisting of low molecular weight polyethyleneglycols (PEG) of 200–600 MW, ($C_2$–$C_8$) mono- and polyalcohols and alcohols of ($C_7$–$C_{18}$) hydrocarbons of a linear or branched configuration said composition comprises in weight % of total composition: polar solvent 77–98%, active compound 1–20%, or where said active compound is soluble in a pharmacologically acceptable non-polar solvent said composition comprises in weight % of total composition: non-polar solvent 5–55% selected from the group consisting of ($C_2$–$C_{24}$) fatty acid ($C_2$–$C_6$) esters, ($C_7$–$C_{18}$) hydrocarbons of a linear or branched configuration, and ($C_2$–$C_6$) alkanoyl esters, and triglycerides of said fatty acids, and active compound 1–20%.

\* \* \* \* \*